United States Patent [19]
Lotz et al.

[11] Patent Number: 5,334,602
[45] Date of Patent: Aug. 2, 1994

[54] ARYLOXALKYLAMINE DERIVATIVES AND USES THEREOF

[75] Inventors: Bernhard Lotz; Gerhard Greier, both of Linz, Austria

[73] Assignee: Laevosan-Gesellschaft GmbH, Linz/Donau, Austria

[21] Appl. No.: 768,535

[22] PCT Filed: Mar. 8, 1990

[86] PCT No.: PCT/EP90/00380

§ 371 Date: Sep. 3, 1991

§ 102(e) Date: Sep. 3, 1991

[87] PCT Pub. No.: WO90/10628

PCT Pub. Date: Sep. 20, 1990

[30] Foreign Application Priority Data

Mar. 8, 1989 [DE] Fed. Rep. of Germany ....... 3907512

[51] Int. Cl.$^5$ ............... A61K 31/165; A61K 31/138; C07C 225/10; C07D 333/32
[52] U.S. Cl. .................... 514/317; 514/326; 514/422; 514/428; 514/445; 514/448; 514/652; 514/821; 546/213; 548/527; 548/571; 549/64; 560/27; 564/349
[58] Field of Search .......... 549/64, 72; 564/346, 564/349; 560/250, 251, 236, 27; 514/821, 445, 448, 651, 317, 326, 422, 428, 652; 546/213; 548/527, 571

[56] References Cited

U.S. PATENT DOCUMENTS

| | | | |
|---|---|---|---|
| 4,352,819 | 10/1982 | Binder | 549/64 |
| 4,425,362 | 1/1984 | Berthold et al. | 519/821 |
| 4,816,604 | 3/1989 | Louis et al. | 564/349 |

FOREIGN PATENT DOCUMENTS

| | | | |
|---|---|---|---|
| 0053603 | 11/1981 | European Pat. Off. | 549/64 |
| 0074014 | 8/1982 | European Pat. Off. | 514/651 |
| 0233173 | 1/1987 | European Pat. Off. | 549/64 |
| 2001431 | 7/1971 | Fed. Rep. of Germany . | |
| 3328376 | 1/1985 | Fed. Rep. of Germany | 514/651 |

OTHER PUBLICATIONS

H. G. Hege, et al., *Arzneim-Forsch*; "Studies on the Meta bolisim of Propagenone," 34(II), (8), pp. 843–849 (1984).

T. Green, "Protective Groups in Organic Synthesis," pp. 222–235, John Wiley & Sons, New York (1981).

R. Neidlein et al., *Arzneim-Forsch*, "Synthesis of Glucuronides of Propafenone . . . ", 38 (II) (9), pp. 1275–1262 (1988).

T. C. Wascher, et al., *Arzneim-Forsch*, "Antiarihythmic Effects of Two New Propafenone Related Drugs," 41 CI) (2), pp. 119–124 (1991).

R. Morrison et al., "Organic Chemistry" 3rd ed., pp. 555 and 673, Allyn cd Bacon, Boston (1973).

*Primary Examiner*—Richard L. Raymond
*Attorney, Agent, or Firm*—Felfe & Lynch

[57] ABSTRACT

New aryloxy-alkylamine derivatives of the general formula I

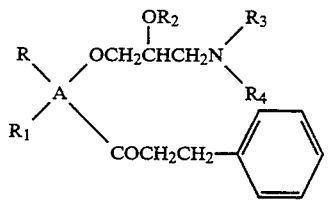

in which A signifies a benzene or thiophene ring, R and $R_1$, independently of one another, each hydrogen, alkyl, halogen, $CF_3$ or alkoxy, $R_2$ alkyl, cycloalkyl, alkenyl, alkynyl, alkaryl or saturated or unsaturated aliphatic or aromatic acyl, $R_3$ and $R_4$ in each case hydrogen, alkyl, alkenyl, alkynyl or cycloalkyl with, in each case, up to 8 C-atoms, whereby $R_3$ and $R_4$ can be the same or different but are not simultaneously hydrogen or $R_3$ and $R_4$, together with the nitrogen atom connecting them, form a 5- to 7-membered saturated ring or a saturated heterocyclic ring which can possibly contain an oxygen or nitrogen atom as a further heteroatom in the ring, whereby an additional nitrogen atom can be substituted by an alkyl radical with up to 3 C-atoms, and their acid-addition salts possess interesting pharmaceutical properties and are especially suitable as anti-arrhythmics.

21 Claims, No Drawings

ARYLOXALKYLAMINE DERIVATIVES AND USES THEREOF

The invention concerns new, therapeutically valuable aryloxy-alkylamine derivatives, their preparation and compositions which contain these derivatives as active material.

In EP 53 603 are described derivatives of 1-[3-(2-hydroxy-3-alkylaminopropoxy)-2-thienyl]-3-phenyl-1-propanone as well as their acid addition salts which are useful as anti-arrhythmic medicaments and, in part, even display properties superior to propafenone.

Similar compounds are also known from DE-OS 33 16 155. They also have the hydroxypropoxy group.

Furthermore, from DE-OS 20 01 431 are known 2-hydroxyalkylaminopropoxyphenylpropiophenone derivatives which are also said to display anti-arrhythmic properties.

In general, these known compounds display satisfactory effectiveness in the case of administration by injection but, in the case of oral administration, they leave something to be desired and require considerably higher dosages for the achievement of satisfactory effectiveness. However, since, as a rule, anti-arrhythmic agents are to be orally administered in order the patient encounter no problems in self-administration, there is a need for active materials with better effectiveness in the case of oral administration.

Surprisingly, it has now been found, that this task can be solved by conversion of the free OH group in the 2-hydroxy-3-aminopropoxy group into an ether or ester group.

Therefore, the subject of the invention are aryloxy-alkylamine derivatives of the general formula I

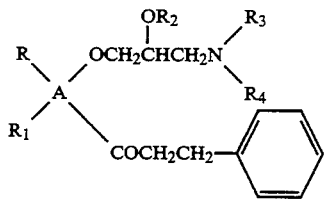

in which A signifies a benzene or thiophene ring, R and $R_1$, independently of one another, are each hydrogen, alkyl, halogen, $CF_3$ or alkoxy, $R_2$ is alkyl, cycloalkyl, alkenyl, alkynyl, alkaryl or saturated or unsaturated aliphatic or aromatic acyl, $R_3$ and $R_4$ are each hydrogen, alkyl, alkenyl, alkynyl or cycloalkyl with, in each case, up to 8 C-atoms, whereby $R_3$ and $R_4$ can be the same or different but are not simultaneously hydrogen or $R_3$ and $R_4$, together with the nitrogen atom connecting them, form a 5- to 7-membered saturated ring or a saturated heterocyclic ring which may contain an oxygen or nitrogen atom as a further heteroatom in the ring, whereby an additional nitrogen atom can be substituted by an alkyl radical with up to 3 C-atoms, as well as their acid-addition salts.

In the substituents R, $R_1$, $R_2$, $R_3$ and $R_4$, the alkyl groups and their unsaturated derivatives and the alkyl radicals in the acyl group contain 1 to 8 C-atoms. The alkyl, alkenyl, alkynyl, alkoxy and acyl groups preferably have 1 to 4 C-atoms. Especially preferred are those compounds of the general formula I in which R and $R_1$ are H or $CH_3$.

By the compounds of the formula I in which A signifies the thiophene ring, especially preferred are those wherein R is hydrogen and $R_1$ is methyl. In the case of the corresponding compounds in which A signifies the benzene ring, especially preferred are those where R and $R_1$ are hydrogen.

Independently of the meaning of A, the isobutyl group is especially preferred for $R_3$.

The compounds according to the invention contain an asymmetric carbon atom and, therefore, when a stereospecific synthesis is not employed, are normally present in the form of a racemate. The racemate can be separated into its isomers according to usual methods. The optically-active isomers are also a subject of the invention.

A further subject of the invention is a process for the preparation of compounds of the general formula I, which is characterised in that one reacts a compound of the general formula II or IIa

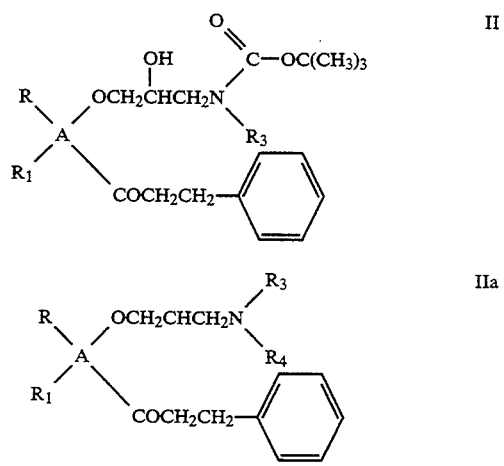

in which A, R, $R_1$, $R_3$ and $R_4$ have the meaning given for formula I, with an alkylation agent, such as an alkyl halide, alkyl sulphuric acid ester or alkyl sulphonic acid ester, or with an acyl halide, in the presence of at least one equivalent of a base in an inert organic solvent, if desired converts the compounds obtained of the general formula III

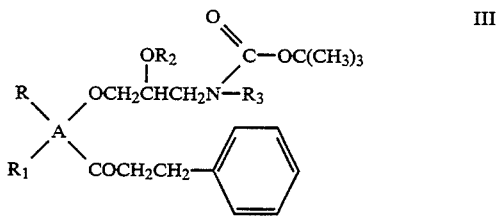

by treatment with acid into the corresponding compounds of the formula I, in which $R_4$ signifies hydrogen, and, if desired, converts the compounds into an acid-addition salt.

The reaction according to the invention is best carried out by dissolving a compound of the formula II or IIa in an inert organic solvent, such as e.g. dimethylformamide (DMF) tetrahydrofuran (THF) diethylether ($Et_2O$) dioxane, and subsequently mixed with at least 1 equivalent of a strong base, preferably an alkali metal hydride or alcoholate. The reaction temperature lies between 0° C. and 40° C. An alkyl transmitter or acyl transmitter is then added at a temperature between 0° C.

and 70° C. In general, the reaction time lies between 50 minutes and 6 hours. By acidolytic splitting off of the tert.-butyloxycarbonyl protective group, preferably with CF₃COOH, the free bases of the general formula I in which R₄ signifies hydrogen are obtained from the compounds of general formula III, in an inert organic solvent. In general, the reaction period lies between 50 minutes and 2 hours at a reaction temperature between about −15° C. and −10° C.

Since the compounds of the general formula I are mostly oils and are both difficult to crystallise, and, for the most part, are not distillable without decomposition, it is recommended that the purification be carried out via readily crystallising acid-addition compounds, such as e.g. hydrochlorides.

To do this, one dissolves the crude base in a suitable solvent, e.g. in a lower alcohol or ether, adds thereto at least an equivalent amount of acid, evaporates off the solvent in a vacuum and then recrystallises the residue from methanol, ethanol or preferably acetone, possibly with the addition of water.

The so-obtained acid-addition salts can then be converted in per se known manner, e.g. with alkalies or ion exchangers, into the free, purified bases from which, by reaction with organic or inorganic acids, especially those which are suitable for the formation of therapeutically usable salts, further salts can be obtained.

As a result of the close relationships between the new compounds and their salts, the following statements apply for both the free bases and for their salts.

The compounds of the general formula II can be prepared, starting from the substances known from the literature of formula IV, in which A, R, R₁ and R₃ have the above meaning (EP 0053603; DE-OS 20 01 431), and the commercially available reagents for the protection of amino functional groups, especially di-tert.-butyl dicarbonate or tert.-butyl carbazate (tert.-butyloxycarbonyl azide), according to processes known to the expert, as follows:

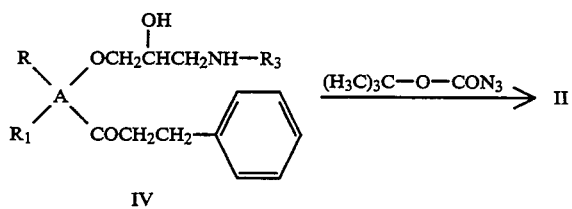

The acid-addition salts of the end compounds can be converted in per se known manner, for example by addition of an alkali or by ion exchangers into the free bases. Other salts can be formed therefrom by reaction with inorganic or organic acids, especially those which are suitable for the formation of a therapeutically usable and pharmaceutically acceptable salt.

Examples of pharmaceutically acceptable salts are the salts of hydrohalic acids, sulphuric acid, phosphoric acids, nitric acid, perchloric acid, as well as of aliphatic, alicyclic, aromatic or heterocyclic carboxylic acids or sulphonic acids, such as formic acid, glutaric acid, acetic acid, propionic acid, butyric acid, isovaleric acid, succinic acid, glycolic acid, lactic acid, pyruvic acid, glyceric acid, malic acid, tartaric acid, citric acid, ascorbic acid, malonic acid, maleic acid, fumaric acid, oxalic acid, tryptophan, lysine, arginine, N-acetylcysteine, mucic acid, hydroxymaleic acid, phenylacetic acid, benzoic acid, p-aminobenzoic acid, p-hydroxybenzoic acid, anthranilic acid, salicylic acid, methanesulphonic acid, ethanesulphonic acid, hydroxyethanesulphonic acid, ethylenesulphonic acids, halobenzenesulphonic acids, toluenesulphonic acid, naphthalenesulphonic acids, sulphanilic acid, methionine, nicotinic acid, possibly picric acid for purification.

However, other acids can possibly also be used.

The new compounds of formula I and their pharmaceutically usable salts display outstanding anti-arrhythmic properties, especially when administered orally.

Therefore, a further subject of the invention is a composition which is characterised by containing at least one compound of the general formula I or a pharmacologically acceptable salt thereof in combination with a usual galenical adjuvant and/or carrier material. Such a composition is suitable for the treatment of diseases of the heart-circulatory system, especially as anti-arrhythmics.

On the basis of these pharmacological properties, the new compounds can be used either as the composition alone or in admixture with other active substances in the form of usual galenical compositions, for treatment of diseases which are caused by heart rhythm disturbances, such as tachycardia.

Among the types of tachycardias which can be treated with the compounds according to the invention are supraventricular and ventricular tachycardias, supraventrical and ventricular ectopias and "reentry" tachycardias.

The compositions according to the invention contain the compounds of the general formula I according to the invention in admixture with a pharmaceutical, organic or inorganic carrier material suitable for enteral or parenteral administration, for example water, gelatin, gum arabic, lactose, starch, magnesium stearate, talc, a vegetable oil, polyalkylene glycols, petroleum jelly or the like.

The compositions can be present in solid form, e.g. as tablets, film tablets, dragees, suppositories, capsules, microcapsules, plasters, or in liquid form, e.g. as solutions, injection solutions, suspensions or emulsions, or in compositions adapted retarded liberation of the active material.

The compositions may be sterilised and/or contain adjuvant materials, such as preserving, stabilising or emulsifying agents, salts for the alteration of osmotic pressure, or buffers.

In particular, such pharmaceutical preparations can contain the compounds according to the invention in combination with other therapeutically valuable materials. With these, the compounds according to the invention can be formulated together with the above-given adjuvant and/or carrier materials to give combination preparations.

The new compounds are preferably contained in a composition according to the invention in a proportion of about 10 to 800 mg./tablet.

A suitable dose for oral administration of the new compound amounts to about 1 to 20 mg./kg. per day but, depending upon the conditions of the patients to be treated, other doses may also be therapeutic. The new compounds can be administered in several doses and by the oral route.

Pharmacological Properties of the Compound According to the Invention

As representative compound, 1-[3-(2-methoxy-3-(2-methylpropylamino)-propoxy]-4-methyl-2-thienyl ]-3- phenyl-1-propanone hydrochloride (derivative 1) was investigated to study its anti-arrhythmic effectiveness. The prolongation of the effective refractory period was used as the criterion for the assessment of the anti-arrhythmic effectiveness. As comparison substances, 1-[3-(2-hydroxy-3-isobutylaminopropoxy)-4-methyl-2-thienyl]-3-phenyl-1-propane hydrochloride (internal designation: LG 83-6-05) and propafenone were used.

The refractory times of various sections of the conducting system and of the atrial and ventricular myocardium were measured by means of a modified Langendorff method and a very high resolution surface ECG.

For the experimental procedure, hearts of guinea pigs of 300–400 g. weight were used which were perfused with oxygen (95%) and $CO_2$ (5%) enriched tyrode (perfusion rate 4 to 6 ml./min.).

Two silver electrodes were placed epicardially on the heart surface of the spontaneously beating, namely on the valve plane. The period of equilibration amounted to 30 minutes. Table 1 shows the results.

TABLE 1

Change of the conduction times in % brought about by 1 μM of substance depending upon the perfusion period.

|  | 15 min. | 30 min. | 45 min. | 60 min. |
| --- | --- | --- | --- | --- |
| Propafenone (comparison) | | | | |
| AH time | **109 ± 2 | **111 ± 2 | **113 ± 2 | **117 ± 4 |
| HV time | **113 ± 3 | **122 ± 7 | *124 ± 11 | *125 ± 10 |
| QRS period | **115 ± 3 | **120 ± 5 | **122 ± 6 | *123 ± 7 |
| LG 83-6-05 (comparison) | | | | |
| AH time | **113 ± 1 | **116 ± 1 | **117 ± 2 | **120 ± 2 |
| HV time | **125 ± 6 | **147 ± 6 | *139 ± 16 | **153 ± 10 |
| QRS period | **114 ± 14 | 116 ± 8 | *118 ± 8 | *116 ± 6 |
| Derivative 1 | | | | |
| AH time | **119 ± 2 | **127 ± 7 | *132 ± 10 | *147 ± 16 |
| HV time | **111 ± 2 | *118 ± 5 | 133 ± 17 | 171 ± 49 |
| QRS period | **138 ± 2 | **179 ± 14 | **176 ± 16 | **185 ± 22 |

Derivative 1 shows, in comparison with LG 83-6-05 and propafenone, a substantially (significantly) greater prolongation of the conduction times, as well as of the AH time and also of the HV time, as well as a prolongation of the QRS period.

Another compound according to the invention, was tested, i.e., 2-(2-methoxy-3-propylaminopropoxy)-3-phenylpropionphenone hydrochloride (derivative 2), using the ouabain-induced arrhythmia in guinea pigs after oral administration. LG 83-6-05 and propafenone served as comparison substances again.

A constant amount of ouabain (20 μg./kg/min.) was infused intraveneously to narcotized animals and the point of time at which the first ventricular extra systole occurred in the ECG recorded.

By pretreatment of the experimental animals with increasing doses, the time is prolonged up to the appearance of the first ventricular extra systole or the dose of ouabain is increased. A dose-action curve can be produced from dose and time.

The following Table 2 shows the action of the oral pretreatment in comparison with the ouabain-induced arrhythmia of the guinea pig. Point of time of the appearance of the first extra systole is expressed in % of the control (average values).

TABLE 2

|  | % after 40 mg./kg. | % after 80 mg./kg. |
| --- | --- | --- |
| propafenone (comparison) | 117 | 145 |
| LG 83-6-05 (comparison) | 101 | 124 |

TABLE 2-continued

|  | % after 40 mg./kg. | % after 80 mg./kg. |
| --- | --- | --- |
| derivative 2 | 121 | 174 |

The above-described results show that the derivatives according to the invention, display substantially stronger action in comparison with the comparable standard substances propafenone and LG 83-6-05 both in terms of their electrophysiological properties on isolated hearts, and on the live animal.

The following Examples explain the invention in more detail.

EXAMPLE 1

1-[3-(2-Methoxy-3-(tert.-butyloxycarbonyl-2-methyl-propylamino)-propoxy)-4-methyl-2-thienyl]-3-phenyl-1-propanone 15 g. (31.5 mMol) 1-[3-(2-hydroxy-3-(tert.-butyloxy-carbonyl-2-methylpropylamino)-propoxy)-4-methyl-2-thienyl]-3-phenyl-1-propanone are dissolved in 140 ml. absolute ether and mixed at 0° C. with 0.80 g. (33.3 mMol) sodium hydride. Thereafter, this is heated under reflux for 55 minutes. Subsequently, the reaction mixture is cooled to 0° C. and, at this temperature, a solution of 4.4 g. (34.9 mMol) dimethyl sulphate in 10 ml. absolute ether added dropwise thereto. After 65 minutes at 0° C. to 5° C., the reaction mixture is emptied into 2N HCl. The phases are separated and the $H_2O$ phase shaken out three times with $CH_2Cl_2$. The combined organic phases are dried over $Na_2SO_4$ and evaporated. There are obtained 22 g. of an orange-yellow oil which is purified column chromatographically.

Column chromatography: silica gel, PE/EtOH=8:1 or, $CH_2Cl_2$/EtOH=60:1

Yield: 13.0 g. colourless oil (84% of theory). $^1$H-NMR ($CDCl_3$):

δ(ppm): 7.24–7.20 (m; 5H; Bz-H); 7.10 (d; 1H; Th-H$_5$); 4.24–3.93 (m; 3H; —OCH$_2$CH); 3.50–3.14 (h; 4H; —CH$_2$NCH$_2$); 3.34 (s; 3H; —OCH$_3$); 2.98–2.69 (m; 4H; —CH$_2$CH$_2$); 2.17 (d; 3H; Th-CH$_3$) 1.83–1.59 (m; 1H; —CH); 1.44 (s; 9H; —OC(CH$_3$)$_3$); 0.86 (d; 6H; —(CH$_3$)$_2$).

1-[3-(2-Methoxy-3-(2-methylpropylamino)-propoxy)-4-methyl-2-thienyl]-3-phenyl-1-propanone hydrochloride A solution of 10 g. (20.4 mMol) 1-[3-(2-methoxy-3(tert.-butyloxycarbonyl-2-methylpropylamino)-propoxy)-4-methyl-2-thienyl]-3-phenyl-1-propanone in 50 ml. absolute methylene chloride is cooled to −15° C.

and mixed with 96.9 g. (0.850 Mol) trifluoroacetic acid (FLUKA, Order No. 91700). Subsequently, it is stirred at −15° C. to −10° C. After 2 hours, it is neutralised, on ice, with a saturated sodium carbonate solution and the phases separated. The H₂O phase is again shaken out twice with methylene chloride and the combined organic phases dried over Na₂O₄ and evaporated. There are obtained 6.8 g. of a yellow oil (85% of theory).

The crude product is dissolved in about 100 ml. absolute ether and mixed, while cooling, with excess etheral hydrochloric acid. The hydrochloride obtained, initially slightly greasy, becomes crystalline and the bright yellow crystals are filtered off with suction. The so obtained about 7.2 g. of crude product are recrystallised from a little acetone with the addition of ether.

Yield: 5.3 g. of colourless crystals (61% of theory)
M.p.: 102°–104° C.

| Microelementary analysis: $C_{22}H_{32}ClNO_3S$ (426.02) | | | |
|---|---|---|---|
| | C | H | N |
| calc.: | 62.03 | 7.57 | 3.29 |
| found: | 62.02 | 7.54 | 3.25 |

¹H-NMR (CDCl₃): δ(ppm): 7.27–7.21 (m; 5H; Bz-H); 7.14 (d; 1H; Th-H₅); 4.30–3.95 (m; 3H; —OCH₂CH); 3.50 (s; 3H; —OCH₃); 3.37–3.12 (h; 4H; —CH₂NCH₂); 2.92–2.68 (m; 4H; —CH₂CH₂); 2.17 (d; 3H; Th-CH₃); 1.98–1.80 (m;1H; —CH); 1.05 (d; 6H; —(CH₃)₂).

EXAMPLE 2

2-[2-Methoxy-3-(tert.-butyloxycarbonyl-propylamino)-propoxy]-3-phenyl-propiophenone 5 g. (11.3 mMol) 2-[2-hydroxy-3-(tert.-butyloxycarbonyl-propylamino)-propoxy]-3-phenyl-propiophenone are dissolved in 50 ml. abs. DMF and mixed at 0° C. with 0.30 g. (12.5 mMol) sodium hydride. Thereafter, it is stirred for 70 minutes at room temperature. Subsequently, the reaction mixture is cooled to 0° C. and a solution of 1.60 g. (12.5 mMol) dimethyl sulphate in 5 ml. absolute DMF added dropwise thereto. After 40 minutes at 0° to 5° C., the reaction mixture is emptied into 2N HCl. The phases are separated and the H₂O phase extracted three times with CH₂Cl₂. The combined organic phases are after drying over Na₂SO₄, evaporated. There are obtained 4.5 g. of an orange oil which is purified column chromatographically. Column chromatography: silica gel, Bz:EE=14:1. The purified oil crystallises in a low-cooling cabinet.

Yield: 2.2 g. of colourless crystals (43% of theory)
M.p.: 53°–55° C.

¹H-NMR (CDCl₃): δ(ppm): 7.62–6.96 (m; 9H; Bz-H); 4.07–3.68 (m; 3H; —OCH2CH); 3.38–3.09 (h; 8H; —CH₂NCH₂ and —CH₂CH₂); 3.30 (s; 3H; —OCH₃); 1.70–1.40 (m; 2H; —CH₂); 1.43 (s; 9H; —OC(CH₃)₃); 0.90 (t; 3H; —CH₃).

2-(2-Methoxy-3-propylamino-propoxy)-3-phenylpropiophenone 8.2 g. (18.0 mMol) 2-[2-methoxy-3-(tert.-butyloxycarbonyl-propylamino)-propoxy]-3-phenylpropiophenone are dissolved in 150 absolute CH₂Cl₂ and cooled to −15° C. Thereafter, it is mixed with 122.9 g. (1.08 Mol) trifluoroacetic acid and stirred for 90 minutes at a temperature between −15° C. and −10° C. Subsequently, with ice cooling, it is neutralised with a saturated sodium carbonate solution and the phases separated. The H₂O phase is shaken out twice with CH₂Cl₂ and the combined organic phases dried over Na₂SO₄/AK and evaporated. There are obtained 5.5 g. of a yellow oil (86% of theory). The crude product is, for hydrochloride formation, dissolved in absolute ether and the solution mixed with cooling, with ethereal hydrochloric acid. The crystalline hydrochloride is filtered off with suction, recrystallised from acetone/ether and dried in a vacuum.

Yield: 5.0 g. of colourless crystals (71% of theory)
M.p.: 109°–111° C.

| Microelementary analysis: $C_{22}H_{30}ClNO_3$ (391.94) | | | |
|---|---|---|---|
| | C | H | N |
| calc.: | 67.42 | 7.72 | 3.57 |
| found: | 67.48 | 7.76 | 3.65 |

¹N-NMR (CDCl₃):
δ(ppm): 7.66–6.91 (m; 9H; Bz-H); 4.20–3.61 (m; 3H; —OCH₂CH); 3.49 (s; 3H; —OCH₃); 3.29–3.04 (m; 8H; —CH₂NCH₂ and —CH₂CH₂); 1.85–1.53 (m; 2H; —CH₂); 0.93 ( t; 3H; —CH₃).

EXAMPLE 3

1-[3-(2-Methoxy-3-diisopropylaminopropoxy)-4-methyl-2-thienyl]- 3-phenyl-1-propanone 4.44 g. (11.0mMol) 1-[3-(2-hydroxy-3-diisopropylaminopropoxy)-4-methyl-2-thienyl ]-3-phenyl-1-propanone are dissolved in 45 ml. absolute dioxane and mixed at room temperature with 0.27 g. (11.3 mMol) NaH. Thereafter, it is warmed for 45 minutes to 40° C. Subsequently, the reaction mixture is cooled to 20° C. and a solution of 1.52 g. (12.1 mMol) dimethyl sulphate in 2 ml. absolute dioxane added dropwise thereto. After 5 h. at room temperature, it is evaporated and the residue partitioned between a saturated Na₂CO₃ solution and ether. The phases are separated and the H₂O phase extracted three times with ethyl acetate. The combined organic phases are dried over Na₂SO₄ and evaporated. There are obtained 4.7 g. of yellow oil which is purified column chromatographically. Column chromatography: silica gel impregnated, PE/EtOAc=4:1.

The 2.3 g. of oily free base obtained are reacted in absolute ether with ethereal hydrochloric acid to give the glassy amorphous hydrochloride.

Yield: 2.2 g. of colourless powder (44% of theory)
M.p.: 38°–42° C.

| Microelementary analysis: $C_{24}H_{36}ClNO_3S.0.42\ H_2O$ (strongly hygroscopic (461.64) | | | |
|---|---|---|---|
| | C | H | N |
| calc.: | 62.44 | 7.86 | 3.03 |
| found: | 62.20 | 8.07 | 3.11 |

¹H-NMR (CDCl)₃ δ(ppm): 7.26–7.20 (m; 5H; Bz-H); 7.02 (d; 1H; ThH₅); 4.40–4.08 (m; 3H; —OCH₂CH); 3.78–3.61 (m; 3H; —CH₂NCH); 3.52 (s; 3H; —OCH₃); 3.42–3.05 (h; 5H; —CH₂CH₂; —NCH); 2.24 (d; 3H; ThCH₃); 1.57–1.28 (m; 12H; —(CH₃)₂).

EXAMPLE 4

2-(2-Methoxy-3-diisopropylaminopropoxy)-3-phenyl-propiophenone 4.78 g. (12.5 mMol) 2-(2-hydroxy-3-diisopropylaminopropoxy)-3-phenylpropiophenone are dissolved in 48 ml. absolute dioxane and mixed with 0.30 g. (12.5 mMol) sodium hydride. Thereafter, it is stirred for 2 hours at 40° C. Subsequently, it is cooled to room temperature and 1.75 g. (13.9 mMol) dimethyl sulphate, dissolved in 4 ml. absolute dioxane, added dropwise thereto at this temperature. After 1.5 h. at 40° C., it is evaporated. The residue is partitioned between a Na$_2$CO$_2$ solution and ether; the H$_2$O phase is shaken out with ether. After drying over Na$_2$SO$_4$ and evaporation, there are obtained 5.3 g. of orange-yellow oil which is purified column chromatographically. Column chromatography: silica gel impregnated, PE/EtOAc=4:1 or silica gel CH$_2$Cl$_2$/EtOH=15:1

Yield: 2.7 g. of pale yellow oil (54.5% of theory)

| Microelementary analysis: C$_{24}$H$_{35}$NO$_3$ (397.56) | | | |
|---|---|---|---|
| | C | H | N |
| calc.: | 75.53 | 8.87 | 3.52 |
| found: | 75.72 | 8.94 | 3.49 |

$^1$H-NMR (CDCl$_3$) δ(ppm): 7.76–6.99 (m; 9H; Bz-H); 4.35–4.07 (m; 2H; —OCH$_2$); 3.59–3.37 (m; 3H; —NCH$_2$; —CH); 3.29 (s; 3H; —OCH$_3$); 3.11–2.56 (h; 6H; —CH$_2$CH$_2$; —N(CH)$_2$); 0.97 (d; 12H; —(CH$_3$)$_2$).

The starting products can be prepared as follows:

1-[3-(2-hydroxy-3-(tert.-butyloxycarbonyl-2-methypropylamino)-propoxy)-4-methyl-2-thienyl]-3-phenyl-1-propanone To a solution, cooled to 10° C., of 11.2 g. (29.8 mMol) 1-[3-(2-hydroxy-3-(2-methylpropylamino)-propoxy)-4-methyl-2-thienyl]-3-phenyl-1-propane in 230 ml. dioxane are added 7.1 g. ( 32.5 mMol ) di-tert.-butyl dicarbonate (FLUKA; 34659). After the dropwise addition of 15 ml. 0.5N NaOH, the reaction mixture is cooled to 2° C. and stirred for 40 minutes at this temperature. Thereafter, it is evaporated under vacuum, the residue taken up in CH$_2$Cl$_2$ and H$_2$O, the phases separated and the H$_2$O phase shaken out three times with CH$_2$Cl$_2$. After drying over Na$_2$SO$_4$ and evaporation there are obtained 13.5 g. of bright yellow oil which crystallises in a deep cooling cabinet. The crystals are used directly in the next step without further purification.

Yield: 13.2 g. of colourless crystals (93% of theory)
M.p.: 47°–50° C.

$^1$H-NMR (CDCl$_3$): δ(ppm): 7.24–7.18 (m; 5H; Bz-H); 7.08 (d; 1H; Th-H$_5$); 4.19–3.90 (m; 3H; —OCH$_2$CH); 3.32–3.09 (h; 4H; —CH$_2$NCH$_2$); 2.90–2.75 (m; 4H; —CH$_2$CH$_2$); 2.54–2.43 (broad, 1H; OH); 2.20 (d; 3H; Th-CH$_3$); 1.79–1.65 (m; 1H; —CH); 1.48 (s; 9H; —OC(CH$_3$)$_3$); 0.89 (d; 6H; —(CH$_3$)$_2$).

2-[2-Hydroxy-3-(tert.-butyloxycarbonylpropylamino)-propoxy]-3-phenylpropiophenone.

To a solution, cooled to 10° C., of 20 g. (58.6 mMol ) 2-(2-hydroxy-3-propylaminopropoxy)-3-phenylpropiophenone in 230 ml. dioxane are added 15.3 g. (70.1 mMol) di-tert.-butyl dicarbonate. After the dropwise addition of 117 ml. 0.5N NaOH, it is cooled to 2° C. and stirred for 50 minutes. Thereafter, it is evaporated under vacuum, the residue taken up in H$_2$O and CH$_2$Cl$_2$, the phases separated and the H$_2$O phase shaken out three times with CH$_2$Cl$_2$. After drying over Na$_2$SO$_4$ and evaporation, there are obtained 24.5 g. of pale yellow oil which crystallises in a deep cooling cabinet and is used in the next step without further purification.

Yield: 24.5 g. of bright yellow crystals (95% of theory)

M.p.: 86°–89° C.

$^1$H-NMR (CDCl$_3$): δ(ppm): 7.54–6.99 (m; 9H; Bz-H); 4.03–3.72 (m; 3H; —OCH CH); 3.37–3.01 (h; 8H; —CH$_2$CH$_2$ and —CH$_2$NCH$_2$); 1.70–1.42 (m; 2H; —CH$_2$); 1.45 (s; 9H; —OC(CH$_3$)$_3$); 0.85 (t; 3H; —CH$_3$).

1-[3-(2-Hydroxy-3-diisopropylaminopropoxy)-4-methyl-2-thienyl]-3-phenyl-1-propanone 25.0 g. (82.7 mMol) 1-[3-(2,3-epoxypropoxy)-4-methyl-2-thienyl]-3-phenyl-1-propanone are mixed with 84 ml. diisopropylamine and heated under reflux for 10 h. Thereafter, it is evaporated and the residue partitioned between a saturated Na$_2$CO$_3$ solution and ether The phases are separated and the aqueous phase extracted with ether. Subsequently, the organic phase is shaken with 2N HCl; the HCl phase is neutralised, with ice-cooling, with 4N HCl and extracted with ether. After drying over Na$_2$SO$_4$, 18.6 g. of oil are obtained which is purified chromatographically.

Yield: 14.8 g. of yellow oil (4.44% of theory)
M.p.: 66°–69° C. (hydrochloride)

$^1$H-NMR (CDCl$_3$): δ(ppm): 7.23–7.19 (m; 5H; Bz-H); 7.10 (d; 1H; Th-H$_5$); 4.32–4.00 (m; 3H; —OCH$_2$CH); 3.47–2.79 (h; 8H; —CH$_2$CH$_2$; —CH$_2$N(CH)$_2$); 2.25 (d; 3H; Th-CH$_3$); 1.46–1.10 (m; 12H; —(CH$_3$)$_2$).

2-(2-Hydroxy-3-diisopropylaminopropoxy)-3-phenylpropiophenone 10.0 g. (35.4 mMol) 2-[2-(2,3-epoxypropoxy)-3-phenylpropiophenone are dissolved in 36 ml. diisopropylamine and subsequently heated under reflux for 10.5 h. Thereafter, it is evaporated and the residue partitioned between a saturated Na$_2$CO$_3$ solution and ether. The ethereal phase is exhaustively extracted with 2N HCl, the HCl phase washed once with ether and four times with CH$_2$Cl$_2$. The CH$_2$Cl$_2$ phase is dried over Na$_2$SO$_4$ and evaporated. The crude product is recrystallised from diisopropyl ether/acetone.

Yield: 6.2 g. of colourless crystals (45.6% of theory)
M.p.: 125°–129° C.

$^1$N-NMH (CDCl$_3$): δ(ppm): 7.70–6.97 (m; 9H; Bz-H); 4.13–3.91 (m; 3H; —OCH$_2$CH); 3.48–4.24 (m; 2H; —NCH$_2$); 3.14–2.42 (m; 6H; —CH$_2$CH$_2$; —N(CH)$_2$); 1.06–0.94 (m; 12H; —(CH$_3$)$_2$).

We claim:
1. A compound of formula

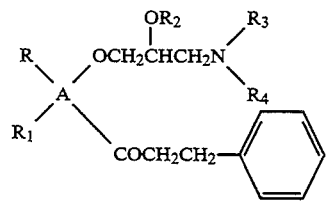

wherein A is a benzene or thiophene ring, R and R$_1$ are each hydrogen, alkyl of 1 to 8 carbon atoms, halogen, CF$_3$ or alkoxy of 1 to 8 carbon atoms, R$_2$ is alkyl of 1 to 8 carbon atoms, cycloalkyl of 1 to 8 carbon atoms, alkynyl of 1 to 8 carbon atoms, or alkaryl of 1 to 8 carbon atoms, R$_3$ and R$_4$ are each hydrogen, alkyl of 1 to 8 carbon atoms, alkenyl of 1 to 8 carbon atoms, alkynyl of 1 to 8 carbon atoms or cycloalkyl of 1 to 8 carbon atoms, whereby R$_3$ and R$_4$ are the same or different but are not both hydrogen, or R$_3$ and R$_4$, together with the nitrogen atom connecting them, form a 5 to 7-membered saturated ring or a saturated heterocyclic ring optionally containing an oxygen or nitrogen atom wherein said optional nitrogen atom is optionally substituted by an alkyl of 1 to 3 carbon atoms, acid addition salts thereof and optically active isomers thereof.

2. The compound according to claim 1, wherein said alkyl, alkenyl, alkynyl and alkoxy have 1 to 4 carbon atoms.

3. The compound according to claim 1 wherein R and $R_1$ are H or $CH_3$.

4. The compound according to claim 3, wherein A is a thiophene ring, R is a hydrogen and $R_1$ is methyl.

5. The compound according to claim 3, wherein A is a benzene ring and R and $R_1$ are hydrogen.

6. The compound according to claim 1 wherein $R_3$ is isobutyl.

7. 1-[3-(2-Methoxy-3-(2-methylpropylamino)-propoxy)-4-methyl-2-thienyl]-3-phenyl-1-propanone.

8. 1-[3-(2-Methoxy-3-(2-methylpropylamino)-propoxy)-4-methyl-2-thienyl]3-phenyl-1-propanone hydrochloride.

9. 2-(2-Methoxy-3-propylaminopropoxy)-3-phenyl-propiophenone.

10. 2-(2-Methoxy-3-propylaminopropoxy)-3-phenyl-propiophenone hydrochloride.

11. Compound selected from the group consisting of: 1-[3-(2-methoxy-3-(tert.-butyloxycarbonyl-2-methyl-propylamino) propoxy)-4-methyl-2-thienyl]-3-phenyl-1-propanone, and 2-[2-methoxy-3-(tert.-butyloxycarbonyl-propylamino)-propoxy]-3-phenyl-propiophenone.

12. Compound selected from the group consisting of: 1-[3-(2-methoxy-3-diisopropylaminopropoxyl)-4-methyl-2-thienyl]-3-phenyl-1-propanone, and 2-(-methoxy-3-diisopropylaminopropoxy)-3-phenyl-propiophenone.

13. A pharmaceutical composition useful for the treatment of anti-arrhythmia in a subject comprising at least one compound of claim 1 or a pharmacologically acceptable salt thereof in combination with a galenical adjuvant or pharmaceutically acceptable carrier.

14. A method of treating or effecting prophylaxis of anti-arrhythmia in a subject which comprises administering to a subject in need thereof a therapeutically effective amount of a compound of claim 1.

15. The method according to claim 14 wherein said alkyl, alkenyl, alkynyl and alkoxy have 1 and 4 carbon atoms.

16. The method according to claim 14 wherein R and $R_1$ are H or $CH_3$.

17. The method according to claim 16 wherein A is a thiophene ring, R is hydrogen and $R_1$ is methyl.

18. The method according to claim 16 wherein A is benzene and R and $R_1$ are hydrogen.

19. The method according to claim 14 wherein $R_3$ is isobutyl.

20. Process for preparing a compound of formula:

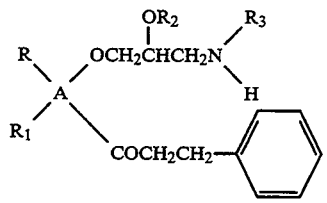

wherein A is a benzene or thiophene ring, R and $R_1$, independently of each other are each hydrogen, C1-C8 alkyl, halogen, $CF_3$, or C1-C8 alkoxy; $R_2$ is C1-C8 alkyl, C1-C8 cycloalkyl, C1-C8 alkynyl, or C1-C8 alkaryl; $R_3$ is C1-C8 alkyl, C1-C8 alkenyl, C1-C8 alkynyl, or C1-C8 cycloalkyl comprising:

reacting a compound of formula:

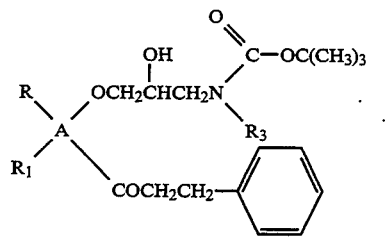

wherein A, R, $R_1$ and $R_3$ are as above with a substance selected from the group consisting of an alkyl halide, alkyl sulphuric acid ester, and alkyl sulphonic acid ester, in the presence of an inert organic solvent containing at least one equivalent of a base, wherein said substance contains a group $R_2$, and $R_2$ is as indicated above, and removing the $COOC(CH_3)_3$ group therefrom to form said compound.

21. The process of claim 20, further comprising treating said compound to form an acid addition salt.

* * * * *

UNITED STATES PATENT AND TRADEMARK OFFICE
CERTIFICATE OF CORRECTION

PATENT NO. : 5,334,602
DATED : August 2, 1994
INVENTOR(S) : Bernhard Lotz, et al.

It is certified that error appears in the above-indentified patent and that said Letters Patent is hereby corrected as shown below:

Column 2, lines 30-35. The formula should be:

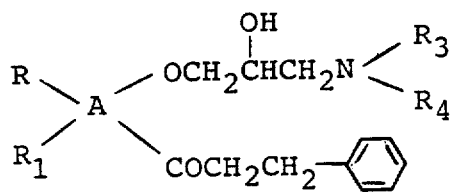

Column 9, line 7: change "$Na_2CO_2$" to -- $Na_2CO_3$ --.

Signed and Sealed this

Fifteenth Day of November, 1994

Attest:

BRUCE LEHMAN

Attesting Officer      Commissioner of Patents and Trademarks